US00PP20992P2

(12) United States Plant Patent
Jacobs

(10) Patent No.: US PP20,992 P2
(45) Date of Patent: May 11, 2010

(54) ***ALSTROEMERIA* PLANT NAMED 'ZAPRIMAT'**

(50) Latin Name: *Alstroemeria hybrida*
Varietal Denomination: Zaprimat

(75) Inventor: Henricus Cornelius Maria Jacobs, Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 0 days.

(21) Appl. No.: 12/321,736

(22) Filed: Jan. 23, 2009

(51) Int. Cl.
*A01H 5/00* (2006.01)

(52) U.S. Cl. ..... Plt./309

(58) Field of Classification Search ..... Plt./309
See application file for complete search history.

*Primary Examiner*—Susan B McCormick Ewoldt
(74) *Attorney, Agent, or Firm*—C. A. Whealy

(57) ABSTRACT

A new and distinct cultivar of *Alstroemeria* plant named 'Zaprimat', characterized by its upright, somewhat outwardly spreading and mounded plant habit; vigorous growth habit; large salmon orange-colored flowers; and good garden performance.

1 Drawing Sheet

Botanical designation: *Alstroemeria hybrida.*
Cultivar denomination: 'ZAPRIMAT'.

BACKGROUND OF THE INVENTION

The present invention relates to a new and distinct cultivar of *Alstroemeria* plant, botanically known as *Alstroemeria hybrida*, commercially used as a garden-type *Alstroemeria* plant, and hereinafter referred to by the name 'Zaprimat'.

The new *Alstroemeria* plant is a naturally-occurring whole plant mutation of *Alstroemeria hybrida* 'Staprivina', disclosed in U.S. Plant Pat. No. 11,692. The new *Alstroemeria* plant was discovered and selected by the Inventor as a single flowering plant from within a population of plants of 'Staprivina' in a controlled greenhouse environment in Rijsenhout, The Netherlands in June, 2002.

Asexual reproduction of the new *Alstroemeria* plant by rhizome divisions in a controlled greenhouse environment in Rijsenhout, The Netherlands since September, 2003, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zaprimat'. These characteristics in combination distinguish 'Zaprimat' as a new and distinct cultivar of *Alstroemeria:*

1. Upright, somewhat outwardly spreading and mounded plant habit.
2. Vigorous growth habit.
3. Large salmon orange-colored flowers.
4. Good garden performance.

Plants of the new *Alstroemeria* differ primarily from plants of the parent, 'Staprivina', primarily in flower color as plants of 'Staprivina' have pink-colored flowers.

Plants of the new *Alstroemeria* can be compared to plants of *Alstroemeria hybrida* 'Staprioxa', disclosed in U.S. Plant Pat. No. 14,075. In side-by-side comparisons conducted in Rijsenhout, The Netherlands, plants of the new *Alstroemeria* differed primarily from plants of 'Staprioxa' in flower color as plants of 'Staprioxa' had red purple-colored flowers.

BRIEF DESCRIPTION OF THE PHOTOGRAPH

The accompanying colored photograph illustrates the overall appearance of the new *Alstroemeria*, showing the colors as true as it is reasonably possible to obtain in colored reproductions of this type. Colors in the photograph may differ slightly from the color values cited in the detailed botanical description which accurately describe the colors of the new *Alstroemeria.*

The photograph comprises a side perspective view of a typical flowering plant of 'Zaprimat' grown in a container.

DETAILED BOTANICAL DESCRIPTION

The aforementioned photograph and following observations and measurements describe plants of the new *Alstroemeria* grown during the summer in 14-cm containers in a glass-covered greenhouse in Rijsenhout, The Netherlands. During the production of the plants, day temperatures ranged from 15° C. to 25° C. and night temperatures ranged from 10° C. to 15° C. Plants used for the photograph and description had been growing for six months. In the following description, color references are made to The Royal Horticultural Society Colour Chart, 1995 Edition, except where general terms of ordinary dictionary significance are used.

Botanical classification: *Alstroemeria hybrida* 'Zaprimat'.

Parentage: Naturally-occurring whole plant mutation of *Alstroemeria hybrida* 'Staprivina', disclosed in U.S. Plant Pat. No. 11,692.

Propagation:

*Type.*—By tissue culture.

*Time to produce a rooted young plant, summer.*—About 40 days.

*Time to produce a rooted young plant, winter.*—About 60 days.

*Root description.*—Fibrous, fleshy, thick; close to 155D in color.

*Rooting habit.*—Freely branching; moderately dense.

*Rhizomes.*—Shape: Elongate; rounded. Length: About 10 cm to 30 cm. Diameter: About 3 mm to 10 mm. Texture: Smooth. Color: Close to 155D.

Plant description:

*Plant and growth habit.*—Upright, somewhat outwardly spreading and mounding plant habit; freely branching habit, bushy appearance; vigorous growth habit.

*Plant height.*—About 17.5 cm to 25 cm.

*Plant diameter* (*spread*).—About 25 cm.

Lateral branch description:

*Aspect.*—Mostly upright.

*Length.*—About 8 cm to 14 cm.

*Diameter.*—About 4 mm to 6 mm.

*Internode length.*—About 2 mm to 40 mm.

*Strength.*—Strong.

*Texture.*—Smooth, glabrous.

*Color.*—Close to 145B; occasional spots, close to 187A.

Foliage description:

*Appearance.*—Leaves asymmetrical; sessile.

*Length.*—About 8.3 cm to 9.9 cm.

*Width: About* 2.4 cm to 3.6 cm.

*Shape.*—Lanceolate.

*Apex.*—Acute.

*Base.*—Attenuate.

*Margin.*—Entire; slightly undulate.

*Texture, upper and lower surfaces.*—Smooth, glabrous.

*Venation pattern.*—Parallel.

*Color.*—Developing and fully developed leaves, upper surface: Close to 147A; venation, close to 147A. Developing and fully developed leaves, lower surface: Close to 147B; venation, close to 147B.

Flower description:

*Flower type and habit.*—Single cup-shaped flowers arranged in compound umbels; flowers face mostly outwardly; perianth segments separate; freely flowering habit.

*Natural flowering season.*—Flowering continuous during the spring in The Netherlands.

*Fragrance.*—None detected.

*Flower longevity on the plant.*—About four weeks; flowers not persistent.

*Flower longevity as a cut flower.*—About 12 to 16 days; flowers not persistent.

*Flower buds.*—Length: About 4 cm to 4.5 cm. Diameter: About 1.2 cm to 1.5 cm. Shape: Roughly ovoid. Color: Close to 185B.

*Umbel height.*—About 9.5 cm to 11 cm.

*Umbel diameter.*—About 12.5 cm to 13 cm.

*Number of flowers per umbel.*—Potentially, about 25.

*Flower diameter.*—About 6.5 cm to 7.5 cm.

*Flower length* (*height*).—About 6.5 cm to 8 cm.

*Flower depth.*—About 6 cm to 7.5 cm.

*Perianth.*—Arrangement: Six arranged in two whorls, each whorl with two lateral and one median segments. Outer perianth, lateral segments: Length: About 5.3 cm to 5.9 cm. Width: About 3.6 cm to 4.2 cm. Shape: Obovate. Apex: Embedded pointed. Base: Attenuate. Margin: Entire; weakly undulate. Texture, upper and lower surfaces: Smooth, glabrous. Color, when opening and fully opened, upper surface: Close to 31B; at the apex, greenish overtones. Color, when opening and fully opened, lower surface: Close to 31B; central blotch, close to 39A; at the apex and venation, faint greenish overtones. Outer perianth, median segment: Length: About 5.6 cm to 6.4 cm. Width: About 3.6 cm to 4.4 cm. Shape: Obovate. Apex: Embedded pointed. Base: Attenuate. Margin: Entire; weakly undulate. Texture, upper and lower surfaces: Smooth, glabrous. Color, when opening and fully opened, upper surface: Close to 31B; at the apex, greenish overtones. Color, when opening and fully opened, lower surface: Close to 31B; central blotch, close to 39A; at the apex and venation, faint greenish overtones. Inner perianth, lateral segments: Length: About 5.9 cm to 6.9 cm. Width: About 2.1 cm to 2.4 cm. Shape: Oblanceolate. Apex: Wishbone-shaped. Base: Attenuate. Margin: Entire; weakly undulate. Texture, upper and lower surfaces: Smooth, glabrous. Color, when opening and fully opened, upper surface: Close to 31B; central blotch, close to 10A; towards the base, close to 29B; stripes, close to 183A. Color, when opening and fully opened, lower surface: Close to 31B; central blotch, close to 10A; towards the base, close to 29B; venation, greenish overtones. Inner perianth, median segment: Length: About 5.2 cm to 6.1 cm. Width: About 2.1 cm to 2.5 cm. Shape: Obovate. Apex: Wishbone-shaped. Base: Attenuate. Margin: Entire; weakly undulate. Texture, upper and lower surfaces: Smooth, glabrous. Color, when opening and fully opened, upper surface: Close to 31B; central blotch, close to 10A; stripes, close to 183A. Color, when opening and fully opened, lower surface: Close to 31B; central blotch, close to 10A; venation, greenish overtones.

*Peduncles.*—Length: About 1.4 to 2.5 cm. Diameter: About 1 mm to 3 mm. Strength: Strong. Angle: Erect to about 20° from vertical. Texture: Smooth, glabrous. Color: Close to 147A with occasional spots, close to 187A.

*Reproductive organs.*—Stamens: Quantity per flower: Six. Anther shape: Elliptical. Anther size: About 5 mm by 7 mm. Anther color: Close to 199A. Pollen amount: Moderate. Pollen color: Close to 199A. Pistils: Quantity per flower: One. Style length: About 2.5 cm to 4.5 cm. Style color: Close to 39A. Stigma shape: Three-parted. Stigma color: Close to 39A. Ovary color: Close to 146B tinted with close to 187A.

*Fruit/seed.*—Fruit and seed development has not been observed.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind, rain and temperatures from about −5° C. to about 40° C.

It is claimed:

1. A new and distinct *Alstroemeria* plant named 'Zaprimat' as illustrated and described.

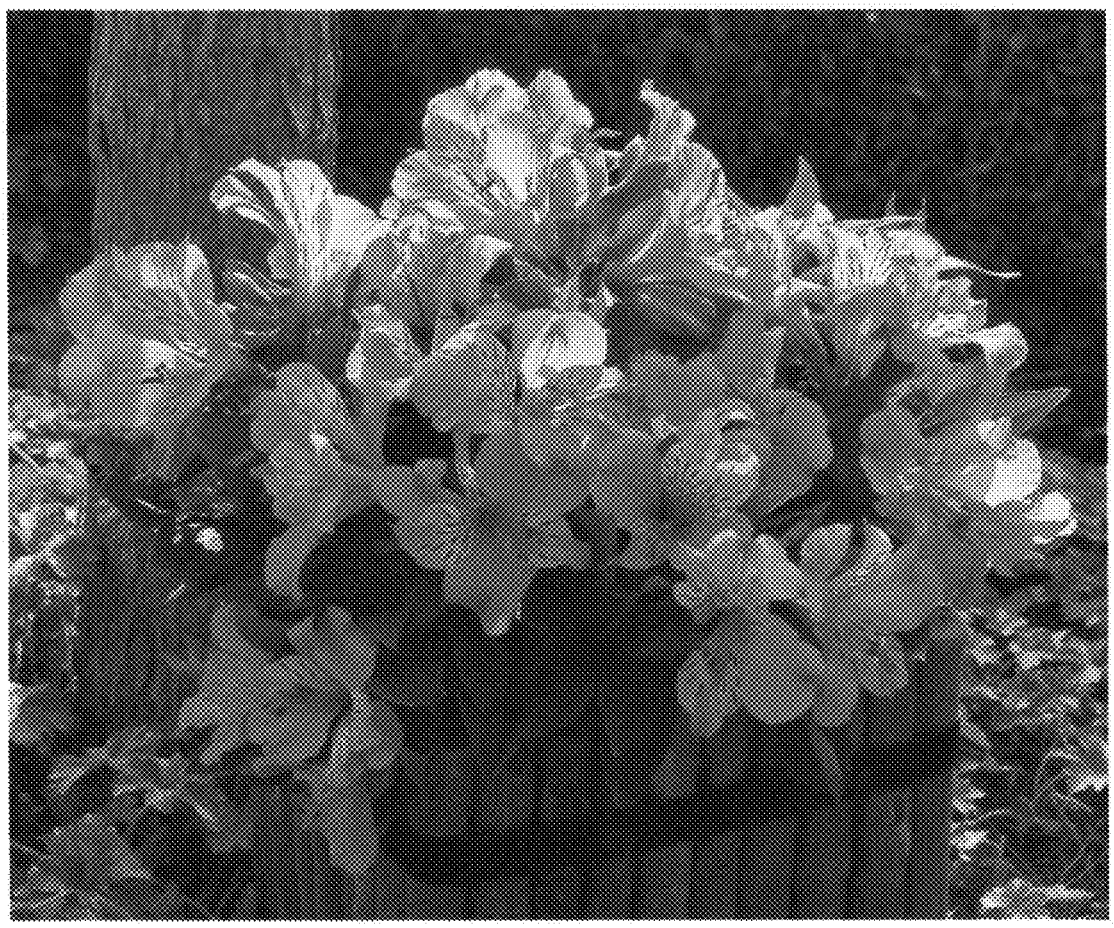

* * * * *